United States Patent [19]

Holman et al.

[11] Patent Number: 5,104,380
[45] Date of Patent: Apr. 14, 1992

[54] SYRINGE WITH DOSE METERING DEVICE

[75] Inventors: Rury R. Holman, Shrublands, Faringdon Road, Cumnor, Oxford, England, OX2 9QY; Jeremy M. J. Marshall, Oxon, England

[73] Assignees: Robert Charles Turner; Rury Reginald Holman; Owen Mumford Limited, all of Oxford, England

[21] Appl. No.: 339,766

[22] Filed: Apr. 18, 1989

[30] Foreign Application Priority Data

Apr. 18, 1988 [GB] United Kingdom .................. 8809115

[51] Int. Cl.$^5$ .............................................. A61M 5/00
[52] U.S. Cl. ..................................... 604/117; 604/157; 604/211; 604/224; 604/232
[58] Field of Search ............... 604/209, 196, 117, 187, 604/232, 134, 208, 211, 192, 218, 220, 224, 228, 136, 138, 156, 157

[56] References Cited

U.S. PATENT DOCUMENTS

| 4,244,366 | 1/1981 | Raines | 604/211 |
| 4,356,822 | 11/1982 | Winstead-Hall | 604/117 |
| 4,373,526 | 2/1983 | Kling | 604/117 |
| 4,484,910 | 11/1984 | Sarnoff et al. | 604/134 |
| 4,592,745 | 6/1986 | Rex et al. | 604/192 |
| 4,710,178 | 12/1987 | Leonard et al. | 604/237 |
| 4,820,287 | 4/1989 | Leonard | 604/204 |
| 4,850,973 | 7/1989 | Jordan et al. | 604/117 |
| 4,883,472 | 11/1989 | Michel | 604/187 |
| 4,921,487 | 5/1990 | Buffet et al. | 604/208 |

FOREIGN PATENT DOCUMENTS 1133555 6/1967 United Kingdom ............... 604/264

Primary Examiner—C. Fred Rosenbaum
Assistant Examiner—Mark Bockelman
Attorney, Agent, or Firm—Millen, White & Zelano

[57] ABSTRACT

A generally pen-like syringe incorporates a dose metering device provided by a cap 7 rotatable with respect to a pen body 8 to a position related to the dose of medicament (for example insulin) to be injected. The rotation compresses a coil spring 6, which is prevented from unwinding by cooperating ratchet teeth. When the dose is to be injected, a trigger slide 42 is moved to the left causing the ratchet teeth to come out of engagement. This permits the spring 6 to unwind, thereby rotating a drive sleeve 1, drive gear 3 and a drive plunger 2. The drive plunger 2 is formed with a quick pitch screw thread so that its rotational movement is accompanied by axial movement to cause medicament to be discharged from a cartridge and injected through a needle.

8 Claims, 3 Drawing Sheets

SYRINGE WITH DOSE METERING DEVICE

BACKGROUND OF THE INVENTION

1. Field of the Invention

The present invention relates to syringes and to a dose metering device for use in conjunction with a syringe and to syringes incorporating such devices.

2. Brief Description of the Background Art

Syringes of pocket pen-like shape and size are known. GB-A-2109690 uses a mechanism operated by rotation of a cap mounted concentrically around the pen barrel. This rotational movement of the externally mounted cap is converted via a rotary ratchet and pawl mechanism and via a lead screw mechanism into axial movement of a rotating screw which drives a plunger down a cartridge in the barrel and expresses the dose. That arrangement permits the provision of a visual scale of micrometer type. The marker can be on the barrel or the cap and the scale on the cap or the barrel. It provides for a large range of doses and for fine gradation between doses. It also provides for the dose to be preset on the scale and then expression to be by a single movement up to a stop. This makes the injection stage independent of any need to assess what dose is being injected.

For some users the actual step of expression the dose causes anxiety and a device which automatically expressed the dose on demand would be attractive. Such a facility also could provide for a more repeatable and smooth injection of the fluid. This could reduce the shock of injection which can occur with some materials.

SUMMARY OF THE INVENTION

According to one aspect of the present invention, a syringe comprises a body and a dose-setting device mounted on the body and capable of being moved to a selected set position, a latch arranged to retain the setting device in the set position, and means arranged to release the latch to cause the set dose to be expelled.

Conveniently, movement of the dose-setting device to the selected set position is accompanied by straining of a spring, which, when the latch is released, provides the force for expelling the set dose.

When the latch is released, the setting device may be returned to an original position to drive a plunger through a one-way clutch to expel the set dose.

Preferably, the dose-setting device is a rotatable cap or ring mounted on the body.

There may be a quick pitch screw thread arrangement for transforming rotation of the setting device into linear movement of the plunger, and then there may be means for automatically releasing the quick pitch screw thread device after discharge of the contents to the syringe.

The body may be adapted for receiving a cartridge containing a fluid to be injected by having a cartridge container removable from the body for insertion of a cartridge and then removal of the cartridge container can be arranged to release the quick pitch screw thread device and allow the plunger to be returned to an initial position.

According to another aspect of the invention, a syringe comprises a body arranged to carry a needle, and a trigger, which trigger can be moved in relation to a body to conceal the needle within a depth adjuster and simultaneously to set a firing spring, and means for firing the spring to move the body so that the needle protrudes beyond the depth adjuster for penetration of a patient's skin.

The operation of the trigger can be arranged automatically to release the latch in the first aspect of the invention, whereby, once the spring has been fired and caused penetration, the dose is automatically expelled through the needle.

The invention has several advantages. It is possible to pre-set the dose using two hands, after which expelling of the dose can be in response to a release or triggering action, which can be achieved using one hand only. Similarly, automatic penetration of the patient's skin by the needle by firing the set spring can be performed using one hand only. Also, many patients would prefer the penetration by the needle to be performed quickly automatically rather than being done manually and slowly. The device also gives a visual indication of the size of the dose being delivered by means of a countdown scale.

BRIEF DESCRIPTION OF THE DRAWINGS

The invention may be carried into practice in various ways, and two embodiments will now be described by way of example with reference to the accompanying drawings, in which.

DESCRIPTION OF THE PREFERRED EMBODIMENTS

Figure 1:
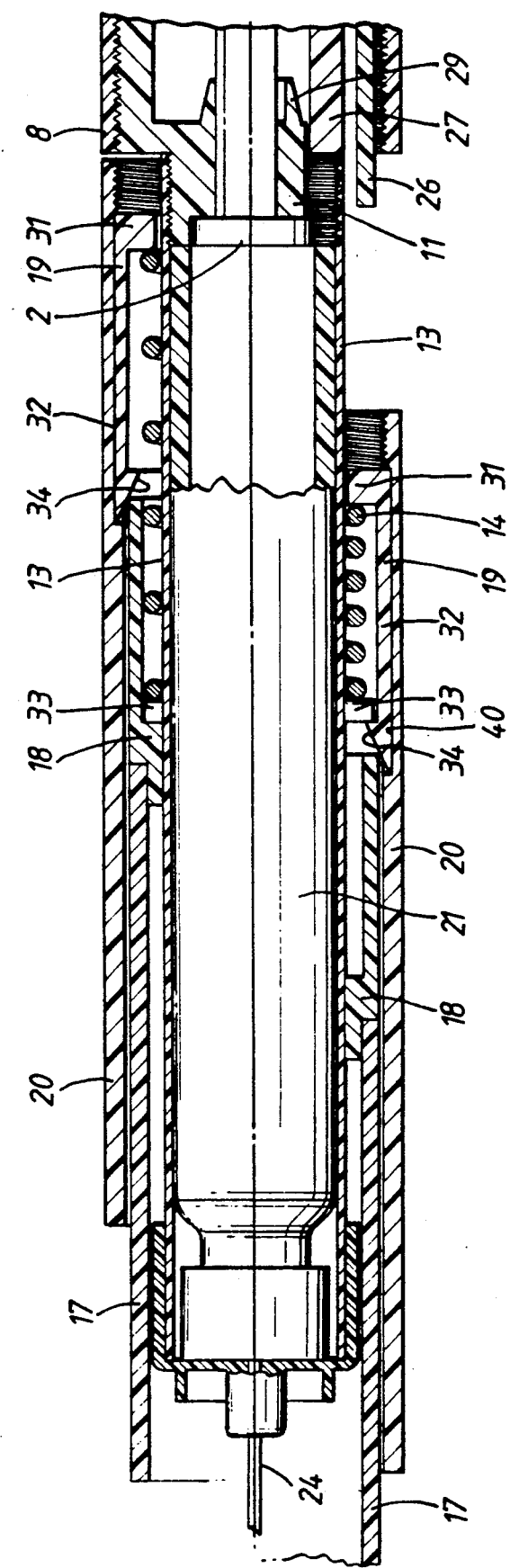
FIG. 1 is a part-sectional part-elevation view through a left-hand portion of a first embodiment of the invention (which is an insulin injector) shown in one particular orientation.

The sections in FIGS. 1 and 2 above and below the centre line are, respectively, on planes at right angles to each other. In FIG. 1, the components below and above the centre line are shown, respectively, in a set position prior to injection and in an injection position after the needle has penetrated the patient.

The syringe is generally pen-like, being of elongate cylindrical form, with a pen body 8 and a latch body 20 extending end to end, and capable of relative longitudinal sliding, as will be discussed below.

Figure 2:
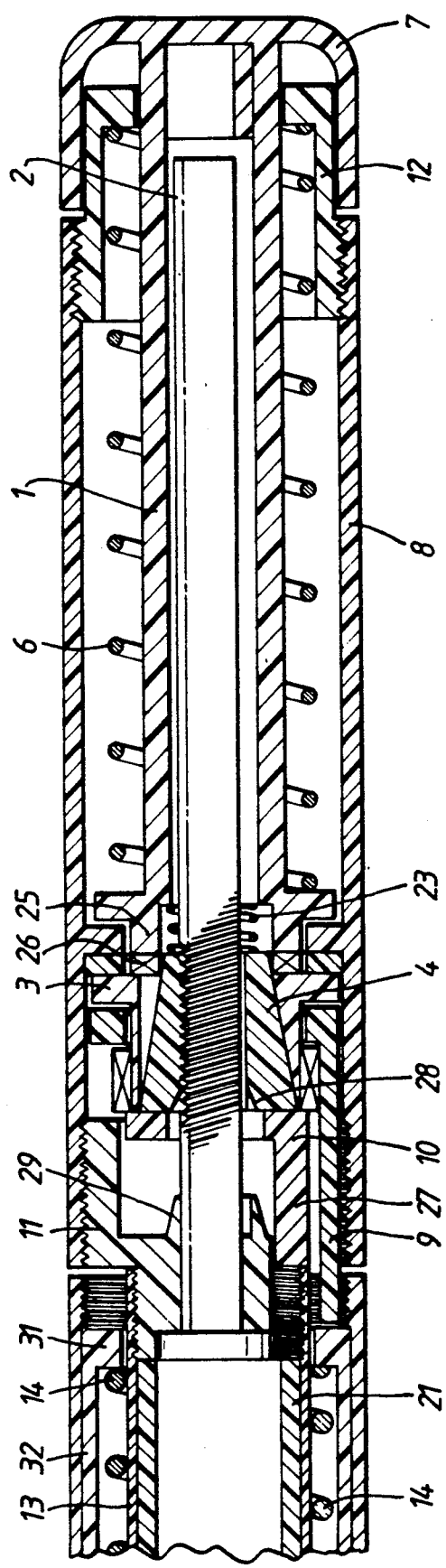
FIG. 2 is a part-sectional part-elevation view through the corresponding right-hand portion.

The pen body 8 is closed at its left-hand end in FIG. 2 by a plunger guide 11 screwed into the pen body and having a cylindrical boss extending to the left and being externally threaded to accommodate a cartridge carrier 13. A cartridge 21 of insulin is fitted into the cartridge carrier 13 before the cartridge carrier is screwed onto the boss on the plunger guide 11.

The guide 11 guides longitudinal movement of a drive plunger 2 from a recess in the end of the plunger guide 11, as shown in FIG. 2, progressively into the open end of the cartridge 21 as insulin is injected through a needle 24 at the end of the carrier 13. The bore in the plunger guide 11 has opposed flats for preventing rotation of the drive plunger 2 as it moves into the cartridge.

Movement of the plunger 2 is achieved by energy stored in a helical spring 6, which is twisted as a pre-set dose of insulin to be injected is set by rotation of a cap 7 which can turn about a graduated sleeve 12 at the right-hand end of the pen body 8. The cap 7 has a window through which graduations can be read to show the angle through which the cap has been turned.

The cap 7 is integral with a drive sleeve 1 which can turn in a plain bearing defined by the sleeve 12 and has an annular ring 25 projecting at its left-hand end and formed with a ring of ratchet teeth. The spring 6 is secured, respectively, at its ends to a flange at the left-hand end of the drive sleeve 1 and a flange on the sleeve 12 so that, as the cap 7 is turned, the spring is strained by being partially wound up.

The spring is a compression spring and both when strained torsionally and unstrained urges the teeth on the annular ring 25 of the drive sleeve into engagement with cooperating ratchet teeth 26 formed on a gear 3. The arrangement of the ratchet teeth is such that the cap and drive sleeve can be turned in relation to the ratchet gear in one direction only with turning being accompanied by a series of clicks, as each successive ratchet tooth is engaged. The ratchet gear 3 is normally held against rotation by engagement of external teeth on the gear 3 with internal teeth on a locking cage 9. The locking cage 9 has legs, on of which is shown at 26, which extend through slots in the plunger guide 11 to prevent rotation of the locking cage in relation to the pen body, although the locking cage can slide axially, as will be described later.

When the pre-set or "dialled up" dose of insulin is to be injected, the locking cage 9 is slid axially out of engagement with the ratchet gear 3 so that the gear can rotate driven by the torque of the spring 6 through the drive sleeve and the ratchet teeth. Rotation continues until the cap has returned to its initial position defined by a positive stop between the cap and the pen body.

Within the ratchet gear 3 are a pair of opposed drive tapers 4 which are externally splined to be capable of axial sliding in relation to the ratchet gear and are internally threaded with a quick pitch thread to cooperate with a corresponding external thread on the stem of the drive plunger 2.

Rotation of the ratchet gear and drive tapers is accompanied by axial movement of the plunger along the quick pitch thread since the plunger stem cannot turn in the plunger guide 11. Thus, the plunger is driven into the cartridge, expelling the pre-set dose of insulin. When the cap stops turning on the pen body, the plunger remains part-way along the inside of the cartridge.

The procedure can be repeated until the cartridge is exhausted, after which the cartridge can be replaced by unscrewing the cartridge carrier 13 from the plunger guide 11.

A reset ring 10 normally holds the drive tapers 4 in the tapered splines in the ratchet gear 3 against a compression spring 23 so that the quick pitch thread drive is normally engaged. However, when the cartridge carrier 13 has been unscrewed from the plunger guide 11, the reset ring 10 can be slid to the left in the Figure by the action of the spring 23 acting through the tapers 4. The reset ring has legs 27 which can slide in the same slots in a plunger guide 11 which accommodate the legs of the locking cage 9.

The tapers are pushed by the spring 23 after the reset ring 10 until a counter-sink 28 formed in the left-hand face of the two joined tapers moves over an inclined projection 29 on the right-hand end of the plunger guide 11. That action opens the tapers so that the quick pitch thread connection with the plunger stem is removed and the plunger can be pushed back into the pen body 8 to the initial position shown in FIG. 2.

After a new cartridge has been inserted in the cartridge carrier, the carrier is screwed back onto the plunger guide and that drives the reset ring 10 back, pushing the drive tapers back into the ratchet gear and into re-engagement with the external threads on the plunger stem.

The latch body 20, which forms a left-hand continuation of the pen body 8, can be slid axially in relation to the pen body 8 and that sliding action carries with it a latch ring 19 having an internal annular ring 31 at its right-hand end and having four circumferentially spaced axially elongate spring fingers 32 extending to the left.

A compression spring 14 acts between the left-hand face of the ring 31 and a ring of four circumferentially spaced projections 33 formed on the cartridge carrier 13, normally urging the latch body against the sliding movement.

As the latch body and latch ring are slid to the left, they also push to the left a trigger sleeve 18 which carries in an outer annular recess, a cylindrical depth adjuster 17.

An inclined cam surface 34 on a projection on the inner face of each finger contacts the right-hand end of the trigger sleeve 18. The projections 33 extend radially outwards into four axially extending internal slots in the end of the trigger sleeve 18, and when they encounter the cam surfaces 34, they lift the fingers 32 radially outwards into slots 40 in the body 20. The fingers 32 are lifted over the projections 33 until, after the trigger sleeve has moved to the left of the projections 33 (the situation shown in the lower half of FIG. 1), the internal projections on the left-hand end of the fingers 32 resite to engage with the left-hand face of the projections 33 on the cartridge carrier 13.

The syringe is then in its latched or set position with the depth adjuster 17 projecting beyond the end of the needle 24.

In this condition, the locking cage 9 is in engagement with the ratchet gear 3 so that the preset dose can be dialled up.

The end of the depth adjuster is placed against the skin of the patient and slight pressure by the operator holding the latch body 20 towards the patient causes the right-hand end of the trigger sleeve to urge the projections on the fingers 32 outwards by a camming action of the cam surfaces 34 so that the compressed spring 14 can then drive the pen body, cartridge carrier and needle to the left until the needle penetrates the skin to the degree determined by the length of the particular depth adjuster 17 which has been chosen.

That action brings the right-hand end of the ring 31 on the latch ring 19 against the left-hand end of the legs 26 on the locking cage 9 which is driven out of engagement with the ratchet gear 3. The ratchet gear 3 then becomes free to rotate as described above, so that the preset dose of insulin is injected.

When the syringe is withdrawn, the latch can be reset and a further dose pre-set.

It will be appreciated that, once the dose has been preset and the syringe has been latched or set, the insulin can be injected using one hand only to hold the latch body against the skin and push it slightly towards the patient. That action not only causes automatic penetration of the skin, but also initiates insertion of the dose.

Figure 3:
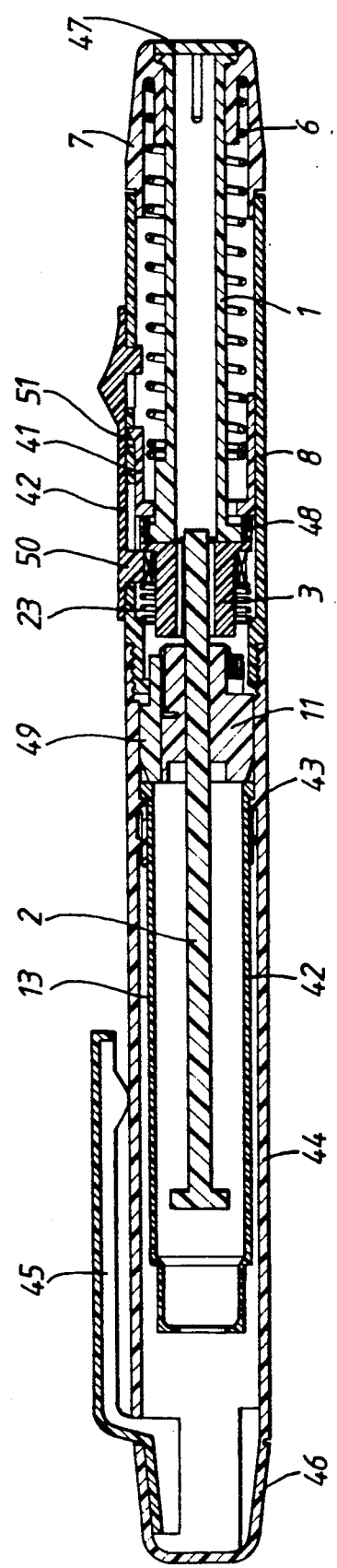
FIG. 3 is a sectional elevation of a simpler injector, which constitutes a second embodiment of the invention.

FIG. 3 is a sectional elevation of the second embodiment of the invention, which, in some ways, is a simplification of the embodiment of FIGS. 1 and 2.

This embodiment only comprises the dose setting device with the latch and release mechanism, and is not provided with the depth adjuster or the means for automatically firing the spring to cause the needle to penetrate the patient. Those two features could be added to the embodiment of FIG. 3, if desired.

The embodiment of FIG. 3 has some components which are similar in operation to components in the embodiments of FIGS. 1 and 2, and those components have been given the same reference numerals.

The dose is preset by turning the cap 7 about the body 1. The cap 7 is fast with an end cap 47 and the drive sleeve 1 and one end of the spring 6. The other end of the spring 6 is locked to a spring retainer 41, which fits inside the body 8 and is keyed against rotation in relation to the body 8 by an external key 51 seated in a notch formed in the body.

At the left-hand end of the drive sleeve 1 an annular flange site within the right-hand end of a drive gear 3 and the flange on the drive sleeve and the drive gear have cooperating ratchet teeth, enabling the drive sleeve to be turned in one direction only in relation to the drive gear, which is keyed against rotation in the body 8 by means of a trigger slide 42 which, in the right-hand position shown in FIG. 3, has an internal spline 50 engaging with an external spline on the drive gear 3. The drive sleeve 1 is a plastics moulding formed integrally at the left-hand end with a circumferentially extending arm having at its free end a radially outwardly extending ratchet tooth, which is urged by the resilience of the arm into engagement with a ring of ratchet teeth on the drive gear 3.

As the cap 7 is turned, the user can count the clicks as the ratchet tooth moves over successive teeth on the drive gear and can also observe the movement of a scale on the cap 7 in relation to a pointer on the body 8 so that he can set the preset dose visually and aurally.

The spring 23 acts in a similar manner as in the embodiment of FIGS. 1 and 2 to urge the trigger slide 42 to the right to maintain its engagement with the drive gear 3 and prevent unwinding of the spring 6 until the dose has been set.

Then, the user can slide the trigger slide 42 to the left as defined by stops at the end of a slot formed in the body 8 so that an internal flange on the trigger slide moves to the left compressing the spring 23 and moving the spline out of engagement with the drive gear 3, which is no longer retained against rotation, so that the spring 6 can unwind rotating the drive sleeve 1 and the drive gear 3. The drive plunger 2 is formed with an integral quick pitch screw thread cooperating with a corresponding internal thread in the bore of the drive gear 3 so that rotation of the drive gear is accompanied by axial movement of the plunger 2 in a similar manner to that described with reference to FIGS. 1 and 2. Rotation continues until an external projection on the drive sleeve 1 comes against a stop consisting of an internal projection formed in the spring retainer 41 when the preset dose will have been discharged from the cartridge by the plunger.

The plunger is prevented from rotation during that movement by two opposed axial flats formed on the plunger and locating in a correspondingly shaped hole in the plunger guide 11, which also acts as a rewind knob. The plunger guide is normally retained against rotation in the body 8 by a locking bar 49 fitted into an axially extending slot in the plunger guide and having an external tooth cooperating with an internal tooth at the left-hand end of the body 8. The locking bar 49 has a radially inwardly extending piece fitted in a notch in the bottom of the slot and acting as a pivot. When the locking bar is unrestrained, the natural position of its left-hand end is radially outwardly of the position shown in FIG. 3 so that the tooth at the right-hand end is pivotted radially inwardly out of engagement with the corresponding tooth at the left-hand end of the body 8. However, when a housing connector 43 is fitted over the plunger guide 11 and the left-hand end of the body 8, it deflects the left-hand end of the plunger bar 49 radially inwardly to the position shown in FIG. 3 in which the tooth at the right-hand end is in engagement with the body 8.

For another dose the cap 7 is turned through the desired number of stops after the trigger slide has been moved by the spring 23 back to the right-hand position, and then when the trigger slide is operated, a further dose is ejected.

This continues until the cartridge is exhausted, after which the cartridge carrier 13 is removed from the body by unscrewing the housing connector 43.

That releases the plunger guide 11 for rotation in relation to the body so that it acts as a rewind knob and can be turned by hand to drive the plunger 2 back to the right to allow a fresh cartridge to be inserted. Then, when the housing connector 43 is re-engaged, the rewind knob is locked in position ready for further operation.

The right-hand end of the drive plunger carries a C clip 48 for defining the extreme left-hand position of the drive plunger.

A removable cover 44 with a cap 46 and a pen type clip 45 are fitted over the left-hand end when the device is not in use.

The device is very simple to use, merely by turning the cap 7 through the desired number of clicks in accordance with the preset dose and then inserting the needle and sliding the slide 42 to the left so that the preset dose is injected.

As mentioned above, the automatic needle injector and spacer can be added to the embodiment of FIG. 3, if desired.

All the components except the springs 6 and 23 may be integral mouldings of appropriate plastics material.

What is claimed is:

1. A syringe for injecting a set dose comprising:
   a body;
   a spring on the body;
   a dose-setting device mounted on the body and connected to the spring, the dose-setting device being moveable to a selected set position against the bias of the spring, wherein movement of the dose-setting device to the selected position is accompanied by straining of the spring;
   a latch on the body arranged to retain the dose-setting device in the set position against the bias of the spring; and
   a latch release means on the body to release the latch to cause the set dose to be expelled from the syringe, the force for expelling the set dose being provided by the spring.

2. A syringe as claimed in claim 1, wherein, when the latch is released, the setting device may be returned to an original position to drive a plunger through a one-way clutch to expel the set dose.

3. A syringe as claimed in claim 1, wherein the dose-setting device is a rotatable cap or ring mounted on the body.

4. A syringe as claimed in claim 1, wherein a quick pitch screw thread arrangement is provided for transforming rotation of the setting device into linear movement of the plunger.

5. A syringe as claimed in claim 4, wherein means are provided for automatically releasing the quick pitch screw thread device after discharge of the contents to the syringe.

6. A syringe as claimed in claim 1, wherein the body is adapted for receiving a cartridge containing a fluid to be injected.

7. A syringe as claimed in claim 1, wherein the body is arranged to carry a needle and wherein the syringe includes a trigger, a depth adjuster and a firing spring, wherein the trigger is moveable in relation to a body to conceal the needle within the depth adjuster and to simultaneously to set the firing spring, and wherein the trigger includes means for firing the firing spring to move the body so that the needle protrudes beyond the depth adjuster for penetration of a patient's skin.

8. A syringe as claimed in claim 7, wherein the operation of the trigger is arranged automatically to release the latch, whereby, once the spring has been fired and caused penetration, the dose is automatically expelled through the needle.

* * * * *